United States Patent
Balavoine et al.

(10) Patent No.: US 6,656,712 B1
(45) Date of Patent: Dec. 2, 2003

(54) METHOD FOR IMMOBILIZING AND/OR CRYSTALLIZING BIOLOGICAL MACROMOLECULES ON CARBON NANOTUBES AND USES

(75) Inventors: Fabrice Balavoine, Paris (FR); Charles Mioskowski, Strasbourg (FR); Patrick Schultz, Fegersheim (FR); Cyrille Richard, Châtenay-Malabry (FR)

(73) Assignees: Commissariat a l'Energie Atomique, Paris (FR); Centre National de la Recherche Scientifique-CNRS, Paris (FR)

( * ) Notice: Subject to any disclaimer, the term of this patent is extended or adjusted under 35 U.S.C. 154(b) by 0 days.

(21) Appl. No.: 09/673,668

(22) PCT Filed: May 7, 1999

(86) PCT No.: PCT/FR99/01086

§ 371 (c)(1),
(2), (4) Date: Dec. 1, 2000

(87) PCT Pub. No.: WO99/57564

PCT Pub. Date: Nov. 11, 1999

(30) Foreign Application Priority Data

May 7, 1998 (EP) .............................................. 98401114
May 25, 1998 (FR) .............................................. 98 06539

(51) Int. Cl.[7] ...................... C12N 11/14; G01N 33/551; C07K 17/14
(52) U.S. Cl. ...................... 435/176; 436/524; 530/391.1
(58) Field of Search ...................... 436/524; 530/391.1; 435/188, 176

(56) References Cited

U.S. PATENT DOCUMENTS 5,866,434 A * 2/1999 Massey et al.

OTHER PUBLICATIONS

Shik Chi Tsang, et al., Angew Chem. Int. Ed. Engl., "Immobilization of Plantinated and Iodinated Oligonucleotides on Carbon Nanotubes", pp. 2198–2200, vol. 36, No. 20, (1997).
S.C. Tsang, et al., J. Chem. Soc., Chem. Commun., pp. 1803–1804, "Immobilization of Small Proteins in Carbon Nanotubes: High–Resolution Transmission Electron Microscopy Study and Catalytic Activity", 1995.
Jason J. Davis, et al., Inorganica Chemica Acta, vol. 272, pp. 261–266, "The Immobilisation of Proteins in Carbon Nanotubes", 1998.
Wolfgang Frey, et al., Proc. Natl. Acad. Sci. USA, vol. 93, pp. 4937–4941, "Two–Dimensional Protein Crystallization Via Metal–Ion Coordination by Naturally Occurring Surface Histidines", May 1996.
Christian Dietrich, et al., Proc. Natl. Acad. Sci. USA, vol. 92 pp. 9014–9018, "Molecular Organization of Histidine–Tagged Biomolecules at Self–Assemblied Lipid Interfaces Using a Novel Class of Chelator Lipids", 1995.
Elizabeth W. Kubalek, et al., Journal of Structural Biology, vol. 113, pp. 117–123, "Two–Dimensional Crystallization of Histidine–Tagged, HIV–1 Reverse Transcriptase Promoted by a Novel Nickel–Chelating Lipid", 1994.

* cited by examiner

Primary Examiner—Mary E. Ceperley
(74) Attorney, Agent, or Firm—Oblon, Spivak, McClelland, Maier & Neustadt, P.C.

(57) ABSTRACT

Method for the attachment and/or crystallization of macromolecules, chemical reagents used in the said method, products obtained as well as applications of the said products in the field of materials and of structural biology, in particular as biosensors or as biomaterials.

The said method comprises essentially the incubation, without stirring, for at least 15 minutes, of a biological macromolecule in solution with nanotubes of carbon closed at their ends, under suitable temperature and pH conditions.

12 Claims, 2 Drawing Sheets

METHOD FOR IMMOBILIZING AND/OR CRYSTALLIZING BIOLOGICAL MACROMOLECULES ON CARBON NANOTUBES AND USES

The present invention relates to a method of attaching and/or crystallizing macromolecules, to the chemical reagents used in the said method, to the products obtained as well as to the applications of the said products in the field of materials and of structural biology, in particular as biosensors or as biomaterials.

The knowledge of the structure of proteins and in particular of their active sites is essential for understanding their mechanism of action. Several methods are available for carrying out such studies: X-rays, NMR, electrocrystalography (2D crystallization).

For carrying out the crystallization proper, the technique of two-dimensional crystallization on a lipid film or monolayer, at the air/water interface (E. E. Ugziris et al., Nature, 1983, 301, 125–129), allows the formation of self-organized systems of biological macromolecules (crystals) and the determination of the structures of these molecules by electron microscopy analysis of the crystals obtained.

This method consists in creating a lipid monolayer at the level of an air/liquid interface, the lipids being selected so as to interact with the proteins, present in the liquid phase, which attach to the lipids and then form an organized network.

The attachment of the proteins to the lipids of the monolayer involves chemical interactions at the level of the polar head of the lipids. These interactions are either aspecific, the lipids possessing charged polar ends, giving rise to crystallization through ionic interactions, or specific. In the latter case, the polar head of the lipids carries ligands exhibiting high affinity with the proteins to be attached.

In particular, it has been possible to show that soluble proteins can two-dimensionally crystallize on lipid films which are charged, or which are functionalized by a ligand for the protein studied (B. J. Jap et al., Ultramicroscopy, 1992, 46, 45–84).

More recently, lipids functionalized by metal complexes such as nickel complexes (E. W. Kubalek et al., J. Struct. Biol., 1994, 113, 117–123) have made it possible to crystallize so-called histidine tagged fusion proteins. These proteins indeed possess, at their N- or C-terminal end, a sequence composed of several histidines. It has been possible to show that the attachment of such proteins to a lipid-nickel was due to a strong interaction between the nickel complex and the poly-histidine sequence (C. Vénien-Brian et al., J. Mol. Biol., 1997, 274, 687–692). Such functionalized lipids have made it possible to obtain crystallization, in particular in the case where an appropriate ligand was not available.

However, the crystallization of proteins on lipid films has the disadvantage of being relatively random and of depending on many factors, which are difficult to control simultaneously:

the ligand carried by the lipids should be sufficiently accessible in order to be able to interact with the proteins. This accessibility depends on the length of the spacer arm between the lipid and the ligand: too short, it gives rise to a penetration of the protein inside the lipid layer; too long, it confers an extremely high degree of freedom on the bound protein and increases the incidence of defects in the crystal;

the lipid monolayer should be sufficiently fluid in order to confer a sufficient lateral and rotational mobility on the bound protein, thus allowing the proteins to organize relative to each other and to develop intermolecular contacts, so as to give rise to the crystal;

another difficulty, inherent to crystallization on a lipid monolayer, relates to the stability of the monolayer; indeed, the stability of the air/liquid interface is difficult to control. In addition, the lipid monolayer should remain stable, not only before the attachment of the proteins, but also after their attachment, in order to allow the spatial organization of the proteins;

for the microscopy study which follows the crystallization step, it is necessary to produce a multitude of planes, because of the planar nature of the structure obtained.

Consequently, the inventors set themselves the aim of providing a method which makes it possible to attach in solution and to optionally induce self-organization of macromolecules which is more suitable for the requirements of practical use than the 2D crystallization methods previously used.

The subject of the present invention is a method for the attachment and/or self-organization of biological macromolecules, characterized in that it essentially comprises the incubation, without stirring, for at least 15 minutes, of a macromolecule in solution with nanotubes of carbon closed at their ends, under suitable temperature and pH conditions.

Nanotubes were discovered in 1991 (S. Ijima, Nature 1991, 354, 54–56); since then, they have generated a lot of interest, in particular because of their mechanical properties: high mechanical resistance (M. M. J. Treacy et al., Nature 1996, 381, pp. 678–680) and electronic properties: conductor or semiconductor property (J. W. G. Wildöer et al., Nature 1998, 391, 59–62: T. W. Odom et al., Nature, 1998, 391, 62–64).

Several methods of preparing nanotubes have been described, including that by T. W. Ebbesen et al. (Nature, 1992, 358, 220–222), which makes it possible to obtain a high yield. Methods of purifying nanotubes have also been described (H. Hiura et al., Adv. Mater., 1995, 7, 275–276; J-M Bonard et al., Adv. Mater., 1997, 9, 827–831 and G. S. Duesberg et al., Chem. Commun. 1998, 435–436); these various methods make it possible to obtain the desired quantities of nanotubes. Methods for the chemical functionalization of nanotubes of carbon have also been described (International Application PCT WO97/32571).

Other methods for the chemical functionalization of nanotubes have also been described; there may be mentioned for example TSANG S. C. et al., Journal of the Chemical Society, Chemical Communications, 1995, 17, 1803–1804 and DAVIS J. J. et al., Inorganica Chimica Acta, 1998, 272, 1, 2, 262–266.

However, they involve chemical reactions which either dramatically modify the geometry of the nanotubes (opening of the ends, partial destruction of the outer sheets), or destroy the intrinsic physical properties of the nanotubes and consequently do not allow organization of biological macromolcules such as proteins, on the nanotubes. Nanotubes modified by such destructive methods are not therefore suitable for adsorption and/or self-organization at their outer surface of synthetic products or of biological macromolecules.

Depending on the technique and the conditions used, several structures of nanotubes may be prepared: the nanotubes have in particular so-called multi-wall nanotube structures (MWNT) or single-wall nanotube structures (SWNT) of graphite. They can be completely, partially or not at all oxidized.

Thus, the nanotubes are, from a chemical point of view, polymers composed solely of carbon and which may comprise up to a million atoms. In accordance with the laws of the chemistry of carbon, the atoms of a nanotube are linked via a solid covalent bond and each atom possesses exactly three neighbours. Thus, regardless of its length, a nanotube is obliged to close at its ends, so as not to leave any chemical bond alone there. In general, its diameter is generally between 1 and 30 nm and its length may be up to several micrometers.

From a physical point of view, nanotubes can be defined as carbon crystals extending in a single direction, the repeating unit having the symmetry of a helix (B. I. Yakobson et al., American Scientist, 1997, 85, 324–337).

According to an advantageous embodiment of the said method, the said biological macromolecules are in particular soluble, membrane or transmembrane proteins, enzymes, antibodies, antibody fragments or nucleic acids.

According to another advantageous embodiment of the said method, the said nanotubes of carbon are functionalized by physical adsorption of a chemical reagent of general formula H-E-L, in which:

H represents a hydrophilic group, selected from the positively or negatively charged groups; ligands or analogues of biological macromolecules, such as, without limitation, biotin, novobiocin, retinoic acid, steroids, antigens; organometallic complexes interacting with amino acids or nucleic acids, such as complexes of copper, zinc, nickel, cobalt, chromium, platinum, palladium, iron, ruthenium or osmium with ligands such as IDA, NTA, EDTA, bipyridine or terpyridine, the said ligands being optionally functionalized with alkyl groups for bonding to E (at the level of X); positively or negatively charged groups are understood to mean, without limitation: ammoniums, carboxides, phosphates, sulphonates; the following groups may be mentioned for example: $-N(CH_3)_3^+$ or $-CO_2-$.

E represents a spacer arm, selected from $C_1$–$C_{10}$ carbon chains, optionally substituted with alkyl groups or otherwise, having unsaturations or polyoxyethylene units which may have or otherwise in the middle of the chain phosphate groups, such as:

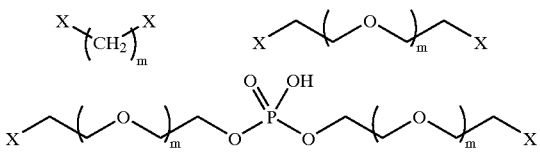

in which:
m represents an integer from 1 to 10,
X represents O, NHCO, OCO, COO, CONH, S, $CH_2$ or NH and constitutes, at the ends of the said carbon chains, organic functions for adhesion of the ester, amide, ether or thioether type;

L represents a lipid unit with one or more chains of variable length, in the form of $C_{12}$–$C_{20}$ having unsaturations or otherwise; an aromatic group of formula $Ar_1$ or of formula $Ar_2$:

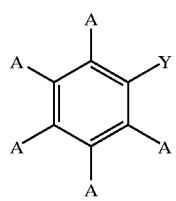

-continued

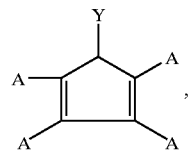

in which:
A represents a hydrogen atom, one of the following groups: alkyl, $CF_3$, $NO_2$, $NH_2$, OH, O-alkyl, S-alkyl, COOH, halogen, an aromatic ring or an aromatic heterocycle in the form of $C_4$–$C_6$, optionally polysubstituted with electron-donating groups of the alkyl type or electron-attracting groups of the $CF_3$ or halide type; L represents for example one of the following aromatic groups: benzyl, naphthyl, anthracenyl, fluoroenyl, tetrabenzofluoroenyl, and
Y represents a bond with E.

For the purposes of the present invention, alkyl is understood to mean linear or branched or optionally substituted $C_1$–$C_6$ alkyl groups.

Surprisingly, both untreated (non-functionalized) nanotubes of carbon and nanotubes of carbon functionalized by non-destructive methods, as defined above, can be used in the method according to the invention.

The functionalization according to the present invention is, surprisingly, non-destructive for the nanotubes; in particular, it avoids the opening of their ends.

It is possible with such a method to adsorb and/or to self-organize at the outer surface of the nanotubes of carbon either synthetic products or biological macromolecules.

Indeed, the present invention makes it possible to induce the formation of arrangements of macromolecules (self-organization) such as proteins, with a helical symmetry.

According to another embodiment of the said method, the said solution consists of a solvent for solubilizing the said biological macromolecules, which is aqueous or aqueous-alcoholic and which optionally contains at least one detergent, depending on the biological macromolecule to be crystallized.

According to another advantageous embodiment of the said method, the incubation conditions are preferably the following: incubation at room temperature, for 15 minutes to 48 hours, at a pH of between 5.5 and 8.5.

Surprisingly, the said method makes it possible to obtain arrangements of biological macromolecules which allow structural studies by electronic microscopy and the preparation of novel nano materials which can be used for their physical, electrical or biological properties.

Such a method has the advantage of making the crystallization of proteins reproducible; in particular, it is easy, in the case where a protein does not crystallize in the presence of nanotubes of a given diameter, to use the method with nanotubes of different diameter; indeed, the crystallization of a given protein depends on the diameter of the nanotubes.

However, in the present invention, it is possible to vary the diameter of the nanotubes and to use equally well multi-wall or single-wall nanotubes of carbon which are completely, partially or not at all oxidized.

Also surprisingly, in the method according to the invention, the attachment or the crystallization of macromolecules on the nanotubes of carbon may be, under the appropriate experimental conditions, as defined above, either spontaneous, that is to say in the absence of any other synthetic products, or induced by addition of a chemical reagent H-E-L, as defined above.

Also surprisingly, the various factors which may come into play in order to allow a reproducible crystallization are, as already specified above, the following: the concentration of the samples, the choice of the solvents, the ionic restraint, the pH of the solutions, the incubation time and the diameter of the nanotubes.

Both the reagents in which L represents a lipid unit with one or more chains of variable length in the form of $C_{12}$–$C_{20}$, having unsaturations or otherwise, and the reagents in which L represents an aromatic group of formula $Ar_1$ or of formula $Ar_2$, make it possible to obtain functionalized nanotubes suitable for the arrangement of macromolecules at their surface; however, the reagents in which L represents an aromatic group of formula $Ar_1$ or of formula $Ar_2$ are particularly preferred.

The subject of the present invention is also bionanomaterials, characterized in that they essentially consist of nanotubes of carbon, on which biological macromolecules are attached by means of non-covalent bonds.

The subject of the present invention is also bionanomaterials, characterized in that they essentially consist of nanotubes of carbon, on which biological macromolecules are self-organized in a crystalline form.

According to an advantageous embodiment of the said bionanomaterials, they are obtained with the aid of a method as defined above.

The subject of the present invention is in addition the applications of the said bionanomaterials to the structural study of the biological macromolecules which are associated with them, as biological reagent and more particularly as immunological reagent and as biosensors or bioconductors.

The subject of the present invention is in addition a chemical reagent capable of being physically adsorbed on nanotubes of carbon, characterized in that it has the general formula H-E-L, in which:

H represents a hydrophilic group selected from the positively or negatively charged groups; ligands or analogues of biological macromolecules; organometallic complexes interacting with amino acids or nucleic acids and whose ligands are optionally functionalized with alkyl groups for bonding to E;

E represents a spacer arm, selected from $C_1$–$C_{10}$ carbon chains, optionally substituted with alkyl groups, having unsaturations or otherwise or polyoxyethylene units which may have or otherwise in the middle of the chain phosphate groups, such as:

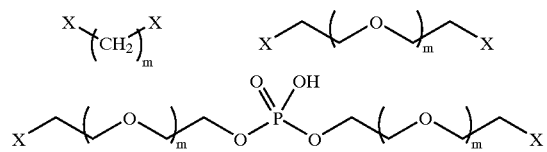

in which:
m represents an integer from 1 to 10,
X represents O, NHCO, OCO, COO, CONH, S, $CH_2$ or NH and constitutes, at the ends of the said carbon chains, organic functions for adhesion of the ester, amide, ether or thioether type;

L represents an aromatic group of formula $Ar_1$ or of formula $Ar_2$:

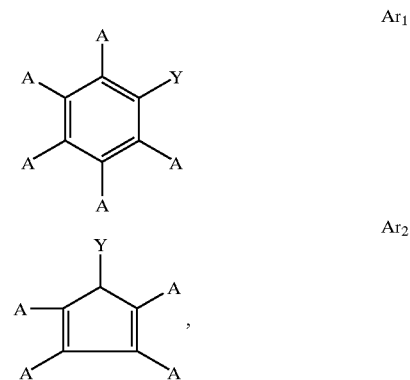

in which:
A represents a hydrogen atom, one of the following groups: alkyl, $CF_3$, $NO_2$, $NH_2$, OH, O-alkyl, S-alkyl, COOH, halogen, an aromatic ring or an aromatic heterocycle in the form of $C_4$–$C_6$, the said rings being optionally polysubstituted with electron-donating groups of the alkyl type or electron-attracting groups of the $CF_3$ or halide type; and
Y represents a bond with E.

According to an advantageous embodiment of the said chemical reagent, it has one of the following structures:

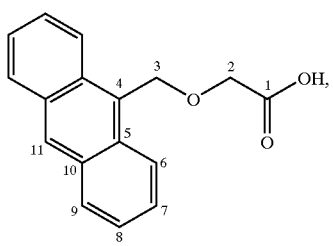

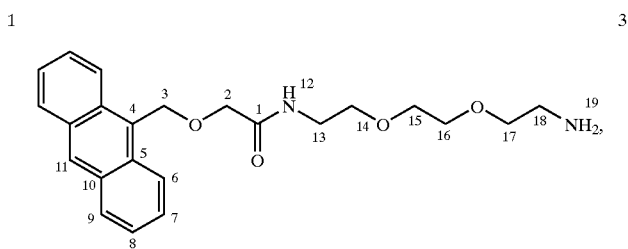

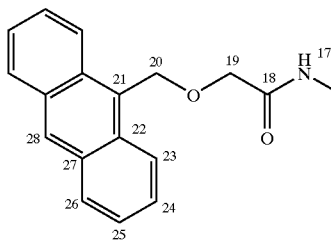

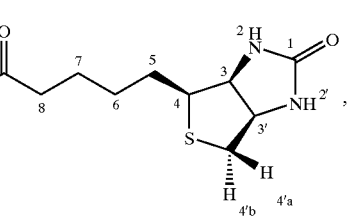

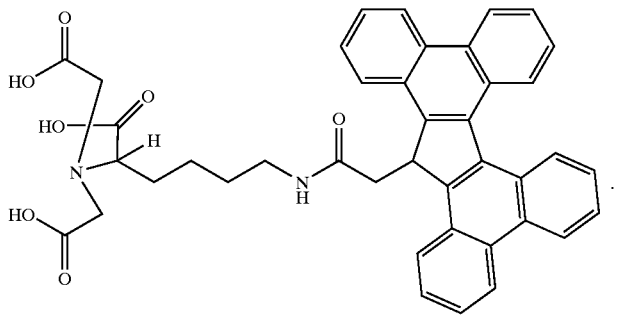

According to another advantageous embodiment of the said chemical reagent, H is selected from the following organometallic complexes:

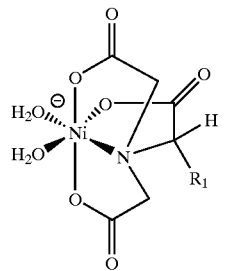
Ni-NTA complex

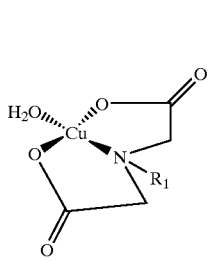
Cu-IDA complex with $R_1$=organic group for bonding to E.

In addition to the preceding arrangements, the invention further comprises other arrangements, which will emerge from the description which follows, which refer to exemplary embodiments of the method which is the subject of the present invention as well as to the accompanying drawings, in which:

Figure 1:
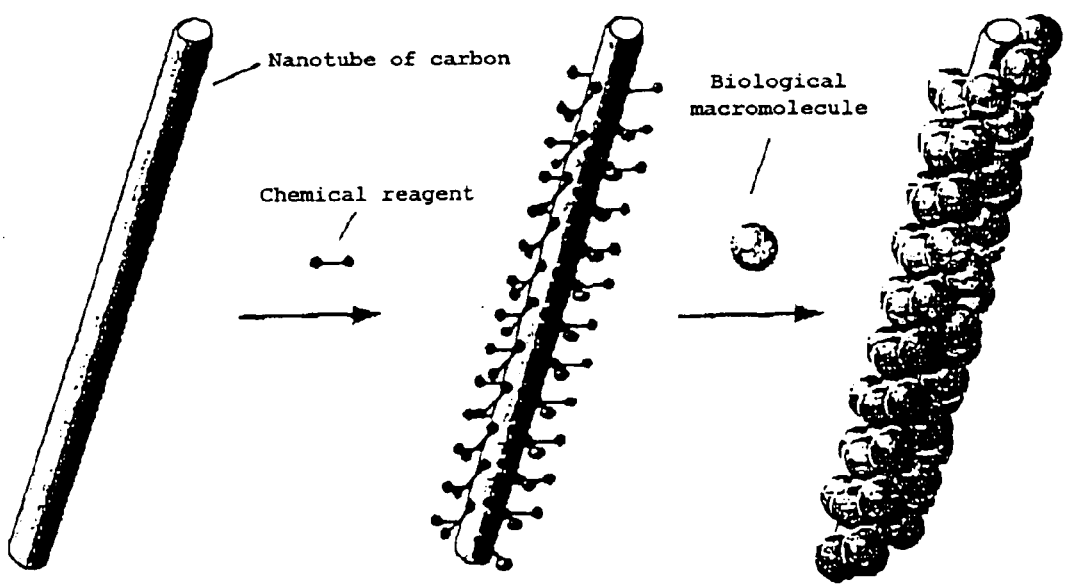
FIG. 1 illustrates the crystallization of a biological macromolecule on a nanotube of carbon, by addition (physical adsorption) of a chemical reagent.
Figure 2:
FIG. 2 illustrates a structure of a chemical reagent used to functionalize, by physical adsorption, the nanotubes of carbon.
Figure 3:
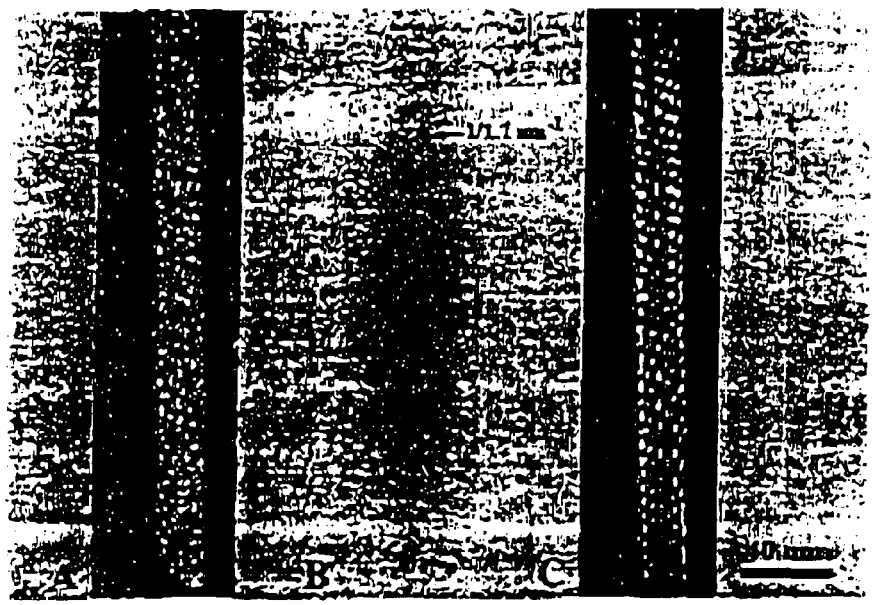
FIG. 3 represents nanotubes with a diameter of close to 10 nm, covered with helical crystals of streptavidin.
Figure 4:
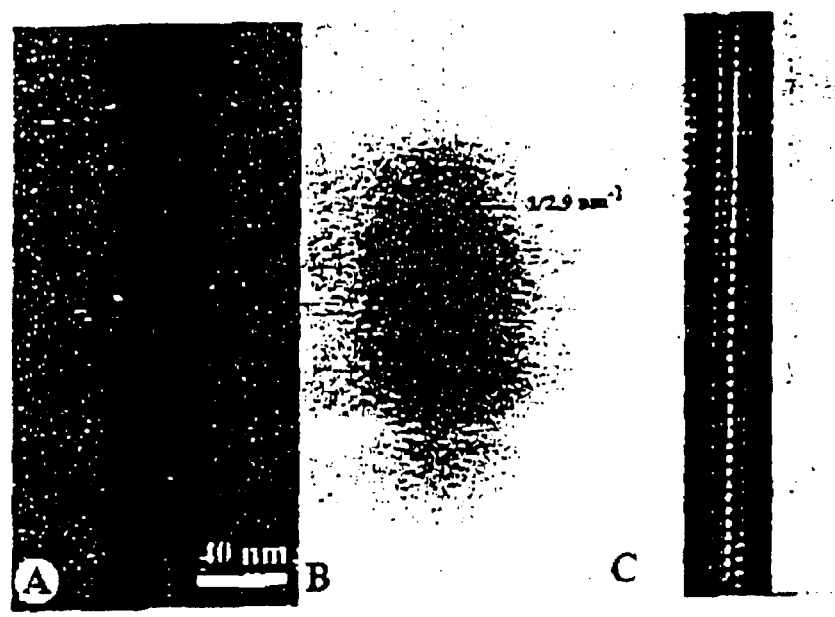
FIG. 4 represents nanotubes covered with helical crystals of HupR protein.

It should be clearly understood, however, that these examples are given solely by way of illustration of the subject of the invention and do not constitute in any manner a limitation thereto.

EXAMPLE 1

Self-organization on Multi-wall Nanotubes of Carbon of Molecules of Streptavidin in the Form of Helical Crystals The multi-wall nanotubes of carbon (MWNT) used are produced by decomposition of a graphite electrode with an electric arc (T. W. Ebbesen et al., *Nature* 1992, Vol. 358, pp. 220–222). After sonication of a solution (2 mg/ml) of nanotubes of carbon, 20 μg of MWNT are collected and dried with an ethane gas stream so as to be finally resuspended in 20 μl of a water/methanol mixture (40% of methanol by volume). After sonication, 20 μl of an aqueous solution of streptavidin (10 μg/ml) are added and the mixture is left, without stirring or vortexing, at room temperature for 45 minutes. 5 μl of the suspension of nanotubes of carbon are then deposited on an electron microscopy grid coated with a carbon film. After negative staining of the sample with a solution of uranyl acetate, the grid is observed in an electron microscope (Philips CM120). It was possible to confirm that the nanotubes with a diameter of close to 10 nm are coated with helical crystals of streptavidin.

EXAMPLE 2

Self-organization on Multi-wall Nanotubes of Carbon of Molecules of "Histidine-tagged" HupR in the Form of Helical Crystals The multi-wall nanotubes of carbon (MWNT) used are produced by decomposition of a graphite electrode with an electric arc (T. W. Ebbesen et al., *Nature* 1992, Vol. 358, pp. 220–222). After sonication of a solution (2 mg/ml) of nanotubes of carbon, 20 μg of MWNT are collected and dried with an ethane gas stream so as to be finally resuspended in 20 μl of aqueous buffer (10 mM Tris; pH=7.5; 350 mM NaCl). After sonication, 20 μl of an aqueous solution of histidine-tagged HupR protein (10 μg/ml) from *Rhodobacter Capsulatus* are added and the mixture is left, without stirring or vortexing, at room temperature for 25 minutes. 5 μl of the suspension of nanotubes of carbon are then deposited on an electron microscopy grid coated with a carbon film. After negative staining of the sample with a solution of uranyl acetate, the grid is observed in an electron microscope (Philips CM120). It was possible to note that a large number of nanotubes are coated with helical crystals of HupR protein.

EXAMPLE 3

Preparation of a Biotinylated Chemical Reagent

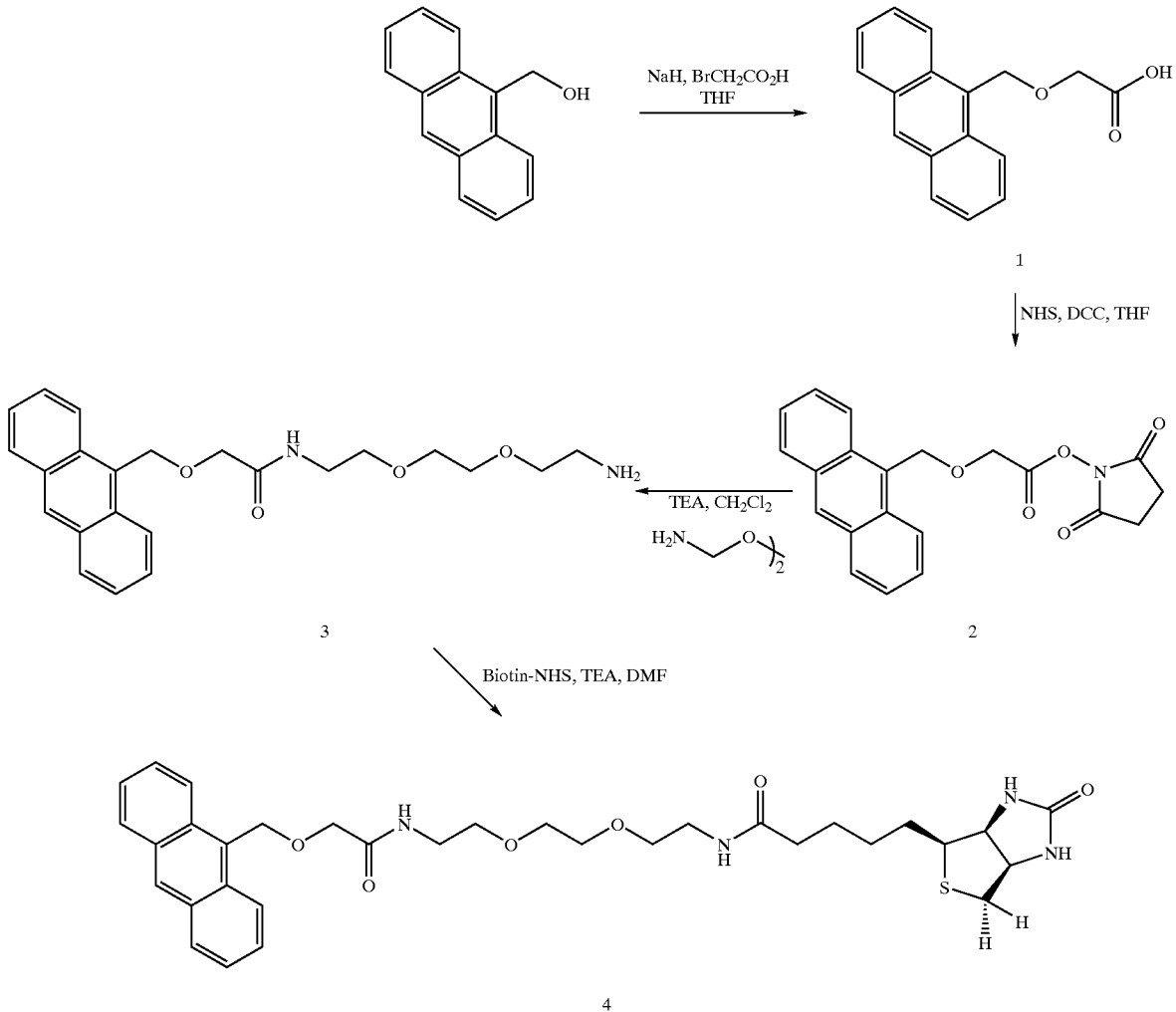

Synthesis scheme

Experimental protocol (Anthracen-9-ylmethoxy)acetic acid 1:

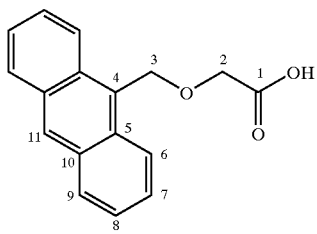

PROCEDURE 2.1 g (10 mmol, 1 eq) of 9-anthracenemethanol in 20 ml of THF are added at 0° C. to a suspension of 1.2 g (30 mmol, 3 eq) of sodium hydride at 60% in oil in 20 ml of THF. The mixture is stirred for one hour under reflux and then the temperature is reduced to 0° C. in order to add 1.4 g (10 mmol, 1 eq) of bromoacetic acid in solution in 20 ml of THF. This solution is further stirred for 5 minutes at 0° C. and then for one hour at room temperature before being heated under reflux for 16 hours. After cooling, the reaction is stopped by addition of 40 ml of a saturated aqueous ammonium chloride solution followed by 10 ml of an aqueous hydrochloric acid solution. The reaction medium is then extracted with twice 50 ml of ether. After drying over sodium sulphate, the organic phase is evaporated to dryness in order to give after chromatography on silica (hexane/EtOAc/AcOH: 70/30/1) 1.212 g of a yellow solid (yield: 45.5%).

EF: $C_{17}H_{14}O_3$ m.p.: 266.299 g/mol; TLC: Rf (EtOAc/Hex/AcOH; 80/20/1): 0.56; $^1$H NMR (300.13 MHz, acetone d6): δ 11.2 (bs, 1H, $H_1$); 8.64 and 8.10 (d and d, 4H, J=8.8 Hz, J=7.9 Hz, $H_6$, $H_9$); 8.61 (s, 1H, $H_{11}$); 7.5–7.7 (m, 4H, $H_7$, $H_8$); 5.68 (s, 2H, $H_3$); 4.41 (s, 2H, $H_2$); $^{13}$C NMR (75.47 MHz, acetone d6): δ 176.27 (1C, $C_1$); 136.51, 136.16 and 133.29 (5C, $C_4$, $C_5$, $C_{10}$); 133.75, 131.10, 130.14 and 129.73 (9C, $C_6$, $C_7$, $C_8$, $C_9$, $C_{11}$); 71.88 (1C, $C_3$); 69.81 (1C, $C_2$): MS (70 eV/DCI/intensity %): m/e: 191 (100, [M–OCH$_2$CO$_2$H]$^+$); 266 (12, [M+1]$^+$); 284 (58, [M+18]$^+$);

2,5-Dioxopyrrolidin-1-yl(anthracen-9-ylmethoxy)acetate 2:

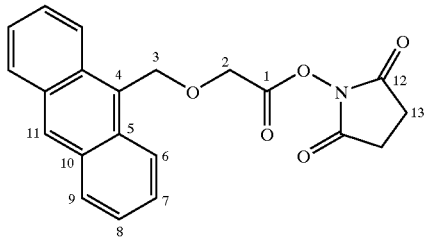

PROCEDURE 510 mg (2.47 mmol, 1 eq) of DCC in solution in 20 ml of THF are added at 0° C. to a solution of 650 mg (2.44 mmol, 1 eq) of (anthracen-9-ylmethoxy)acetic acid 1 and 300 mg of NHS (2.61 mmol, 1.07 eq) in 30 ml of THE. The mixture is stirred overnight at room temperature. The reaction medium is then filtered and then evaporated. The residue obtained is taken up in 50 ml of absolute ethanol in order to give after filtration 727 mg of 2,5-dioxopyrrolidin-1-yle (anthracen-9-ylmethoxy)acetate 2 in the form of a white solid (yield: 82%).

EF: $C_{21}H_{17}NO_5$ m.p.: 363.374 g/mol; TLC: Rf (EtOAc/Hex; 50/50): 0.33; $^1$H NMR (300.13 MHz, CDCl$_3$): δ 8.51 (s, 1H, $H_{11}$); 8.42 and 8.02 (d and d, 4H, J=9.0 Hz, J=8.4 Hz, $H_6$, $H_9$); 7.59 and 7.48 (dd and dd, 4H, $H_7$, $H_8$); 5.71 (s, 2H, $H_3$); 4.53 (s, 2H, $H_2$); 2.90 (s, 4H, $H_{13}$); $^{13}$C NMR (75.47 MHz, CDCl$_3$): δ 168.49 (2C, $C_{12}$); 166.16 (1C, $C_1$); 131.13, 128.94 and 126.36 (5C, $C_4$, $C_5$, $C_{10}$); 128.82, 126.51, 124.88 and 123.83 (9C, $C_6$, $C_7$, $C_8$, $C_9$, $C_{11}$); 65.28 (1C, $C_3$); 64.57 (1C, $C_2$); 25.39 (2C, $C_{13}$); MS (70 eV/DCI/intensity %): m/e: 381 (100, [M+18]$^+$);

N-{2-[2-(2-Aminoethoxy)ethoxy]ethyl}-2-(anthracen-9-ylmethoxy)acetamide 3:

PROCEDURE 1.75 ml of TEA and 91 mg (0.25 mmol, 1 eq) of 2,5-dioxopyrrolidin-1-yl (anthracen-9-ylmethoxy) acetate 2 in solution in 5 ml of CH$_2$Cl$_2$ are added to a solution of 370 mg (2.50 mmol, 10 eq) of 2,2'-(ethylenedioxy)diethylamine in 20 ml of CH$_2$Cl$_2$. The mixture is stirred for 7 hours at room temperature. The reaction medium is then evaporated. The residue obtained is washed with 50 ml of water and then 50 ml of an aqueous potassium hydroxide solution (0.1 N). The organic phase is dried, evaporated and concentrated under vacuum to give after chromatography on silica (CH$_2$Cl$_2$/MeOH/TEA; 90/10/1), 55 mg of N-{2-[2-(2-aminoethoxy)ethoxy]ethyl}-2-(anthracen-9-ylmethoxy) acetamide 3 in the form of a yellow oil (yield: 55%).

EF: $C_{23}H_{28}N_2O_4$ m.p.: 396.491 g/mol; TLC: Rf (CH$_2$Cl$_2$/MeOH/TEA; 90/10/1): 0.28; $^1$H NMR (300.13 MHz, CDCl$_3$): δ 8.44 (s, 1H, $H_{11}$); 8.29 and 7.98 (d and d, 4H, J=9.0 Hz, J=8.4 Hz, $H_6$, $H_9$); 7.53 and 7.45 (dd and dd, 4H, $H_7$, $H_8$); 6.93 (t, 1H, $J_{6-9}$=5.4 Hz, 1H, $H_{12}$); 5.51 (s, 2H, $H_3$); 4.13 (s, 2H, $H_2$); 3.3–3.5 (m, 8H, $H_{14}$, $H_{15}$, $H_{16}$, $H_{17}$); 3.25 (t, J=5.1 Hz, 2H, $H_{13}$); 2.7–2.8 (m, 2H, $H_{19}$); 2.64 (t, 2H, J=5, 1 Hz, $H_{18}$); $^{13}$C NMR (75.47 MHz, CDCl$_3$): δ 169.49 (1C, $C_1$); 131.11, 130.73 and 127.08 (5C, $C_4$, $C_5$, $C_{10}$); 128.92, 128.69, 126.39, 124.87 and 123.64 (9C, $C_6$, $C_7$, $C_8$, $C_9$, $C_{11}$); 72.10, 69.89, 69.78, 69.47 and 69.33 (5C, $C_3$, $C_{14}$, $C_{15}$, $C_{16}$, $C_{17}$); 65.15 (1C, $C_2$); 41.03 (1C, $C_{13}$); 38.31 (1C, $C_{18}$) MS (70 eV/DCI/intensity %): m/e: 397 (100, [M+1]$^+$);

N-{2-[2-(2-(Aminobiotin)ethoxy)ethoxy]ethyl}-2-(anthracen-9-ylmethoxy)acetamide 4:

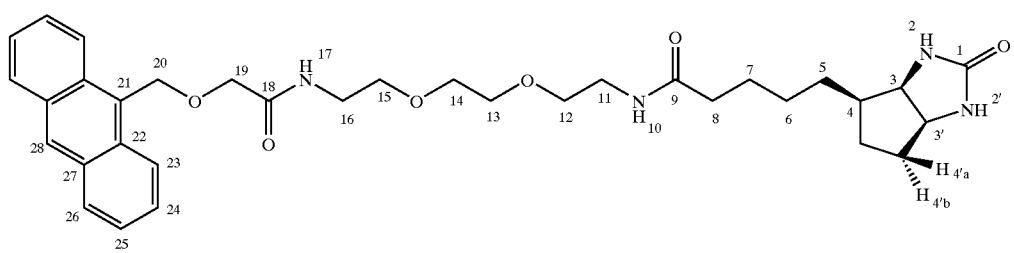

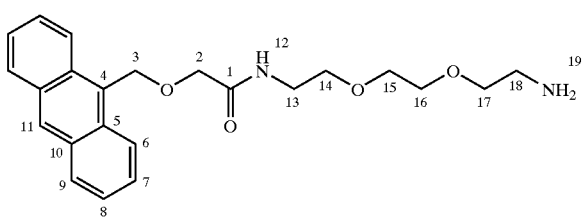

PROCEDURE 1 ml of TEA and 40 mg (0.12 mmol, 1.2 eq) of biotin-NHS in solution in 5 ml of DMF are added to a solution of 40 mg (0.1 mmol, 1 eq) of N-{2-[2-(2-aminoethoxy)ethoxy]ethyl}-2-(anthracen-9-ylmethoxy)acetamide 3 in 5 ml of DMF. The mixture is stirred for 16 hours at room temperature. The reaction medium is concentrated under vacuum in order to give after chromatography on silica (CH$_2$Cl$_2$/MeOH/TEA; 95/5/1), 55 mg of N-{2-[2-(2-(aminobiotin)ethoxy)ethoxy]ethyl}-2-(anthracen-9-ylmethoxy)acetamide 4 in the form of a yellow oil (yield: 89%).

EF: $C_{33}H_{42}N_4O_6S$ m.p.: 622.793 g/mol; TLC: Rf (CH$_2$Cl$_2$/MeOH; 90/10): 0.5; $^1$H NMR (300.13 MHz, CDCl$_3$): δ 8.48 (s, 1H, H$_{28}$); 8.31 and 7.01 (d and d, 4H, J=9.0 Hz, J=8.4 Hz, H$_{23}$, H$_{26}$); 7.55 and 7.47 (dd and dd, 4H, H$_{24}$, H$_{25}$); 6.89 (t, 1H, J$_{16-17}$=5.0 Hz, H$_{17}$); 6.90 (s, 1H, H$_2$); 6.53 (t, 1H, J$_{10-11}$=5.0 Hz, H$_{10}$); 5.67 (s, 1H, H$_{2'}$); 5.55 (s, 2H, H$_{20}$); 4.31 (m, 1H, H$_3$); 4.17 (s, 2H, H$_{19}$); 4.15 (m, 1H, H$_{3'}$) γ; 3.2–3.5 (m, 12H, H$_{11}$, H$_{12}$, H$_{13}$, H$_{14}$, H$_{15}$, H$_{16}$); 2.97 (dt, 2H, H$_4$); 2.75 (dt, 1H, J$_{3'-4'a}$=4.8 Hz, J$_{4'a-4'b}$=12.7 Hz, H$_{4'a}$); 2.2 (d, 1H, J$_{4'a-4'b}$=12.7 Hz, H$_{4'b}$); 2.08 (t, 2H, J$_{7-8}$=7.4 Hz, H$_8$); 1.2–1.7 (m, 6H, H$_5$, H$_6$, H$_7$); $^{13}$C NMR (75.47 MHz, CDCl$_3$): δ 173.00 (1C, C$_1$); 169.56 (1C, C$_{18}$); 163.76 (1C, C$_9$); 131.14, 130.73 and 127.05 (5C, C$_{21}$, C$_{22}$, C$_{27}$)); 128.98, 128.75, 126.45, 124.93 and 123.59 (9C, C$_{23}$, C$_{24}$, C$_{25}$, C$_{26}$, C$_{28}$); 69.74, 69.55, 69.23 and 65.25 (6C, C$_{12}$, C$_{13}$, C$_{14}$, C$_{15}$, C$_{19}$, C$_{20}$); 61.50 and 59.88 (2C, C$_3$, C$_{3'}$); 55.32 (1C, C$_4$); 40.18 (1C, C$_{4'}$); 38.76, 38.33 and 35.65 (3C, C$_8$, C$_{11}$, C$_{16}$); 27.95 and 27.81 (2C, C$_5$, C$_7$); 25.30 (1C, C$_6$); MS (70 eV/DCI/intensity %): m/e: 623 (100, [M+1]$^+$); 640 (8, [M+18]$^+$);

EXAMPLE 4

Physical Adsorption on Nanotubes of Carbon of a Chemical Reagent, Called Hereinafter CR174, Having the Structure H-E-L Protocol: 1 to 20 μl of a solution of chemical reagent called CR174 and whose chemical formula is illustrated below, (1 mg/ml) in methanol are added to 20 μl of a solution of nanotubes of carbon (10 mg/ml in methanol), freshly sonicated. The mixture is then stirred by sonication and then evaporated to dryness by a stream of ethane gas. 40 μl of Tris buffer (20 mM, pH 7.5; 50 mM NaCl) are added to the dry nanotubes of carbon and the suspension is remixed by sonication. The suspension may be optionally centrifuged and washed several times with 500 μl of buffer in order to remove the excess reagent not adsorbed on the nanotubes of carbon.

The physical adsorption of the reagent CR174 on the nanotubes of carbon was able to be demonstrated by electron microscopy with positive staining. The presence of molecules of reagents on the nanotubes of carbon results in the appearance of black spots. These black spots are absent in the absence of the chemical reagent CR174 (or 5).

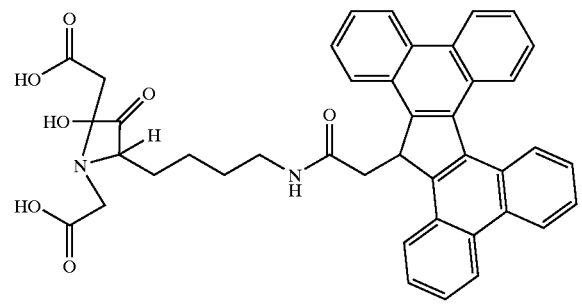

As is evident from the preceding text, the invention is not at all limited to its embodiments, implementations and applications which have just been described more explicitly; on the contrary, it encompasses all the variants which may occur to a specialist in this field, without departing from the framework or the scope of the present invention.

What is claimed is:

1. A method for the attachment of proteins to, and crystallization of proteins on carbon nanotubes comprising:
preparing a solution of said proteins in an aqueous or aqueous-alcoholic solvent at a pH ranging from 5.5 to 8.5, and
contacting without stirring nanotubes of carbon, which are closed at their ends, with said solution for 15 minutes to 48 hours at room temperature.

2. The method of claim 1, wherein the proteins are selected from the group consisting of soluble proteins, membrane proteins, transmembrane proteins, enzymes, antibodies, and antibody fragments.

3. A bionanomaterial obtained by the method of claim 1.

4. The method of claim 1, wherein said aqueous or aqueous alcoholic solvent comprises at least one detergent.

5. The method of claim 1, wherein the diameter of said carbon nanotubes ranges from 1 to 30 nm.

6. The method of claim 1, wherein said proteins are present in an aqueous-alcoholic solvent.

7. The method of claim 1, wherein said proteins are soluble proteins.

8. The method of claim 1, wherein said proteins are membrane proteins.

9. The method of claim 1, wherein said proteins are transmembrane proteins.

10. The method of claim 1, wherein said proteins are enzymes.

11. The method of claim 1, wherein said proteins are antibodies.

12. The method of claim 1, wherein said proteins are antibody fragments.

* * * * *